United States Patent
Zhang et al.

(10) Patent No.: US 9,353,413 B2
(45) Date of Patent: May 31, 2016

(54) INTERNAL REFERENCE GENES FOR MICRORNAS NORMALIZATION AND USES THEREOF

(75) Inventors: Chenyu Zhang, Beijing (CN); Xi Chen, Beijing (CN)

(73) Assignee: Micromedmark Biotech Co., Ltd., Beijing (CN)

( * ) Notice: Subject to any disclaimer, the term of this patent is extended or adjusted under 35 U.S.C. 154(b) by 0 days.

(21) Appl. No.: 14/372,143

(22) PCT Filed: Jan. 13, 2012

(86) PCT No.: PCT/CN2012/070330
§ 371 (c)(1),
(2), (4) Date: Sep. 11, 2014

(87) PCT Pub. No.: WO2013/104131
PCT Pub. Date: Jul. 18, 2013

(65) Prior Publication Data
US 2015/0011413 A1    Jan. 8, 2015

(51) Int. Cl.
*C12Q 1/68* (2006.01)
*C12N 15/11* (2006.01)

(52) U.S. Cl.
CPC ............ *C12Q 1/6876* (2013.01); *C12N 15/111* (2013.01); *C12Q 1/6874* (2013.01); *C12N 2310/141* (2013.01); *C12N 2320/10* (2013.01); *C12Q 2600/158* (2013.01); *C12Q 2600/166* (2013.01); *C12Q 2600/178* (2013.01)

(58) Field of Classification Search
None
See application file for complete search history.

(56) References Cited

U.S. PATENT DOCUMENTS

| 7,993,831 B2 | 8/2011 | Latham et al. | |
| 2009/0075258 A1* | 3/2009 | Latham et al. | 435/6 |
| 2012/0157337 A1* | 6/2012 | Keller et al. | 506/9 |

FOREIGN PATENT DOCUMENTS

| CN | 101818202 | 9/2010 |
| WF | 2008/073922 | 6/2008 |

OTHER PUBLICATIONS

Y. Jin et al., "A Novel Normalization Approach for MicroRNA Quantitative PCR," Progress in Biochemistry and Biophysics, 2011, vol. 38, No. 5, p. 473-481.
J. Wu et al., "Selection of control genes in Real2time qPCR analysis of gene expression in Aedes albopictus," Chinese Journal of Zoonoses, 2011, vol. 27, No. 5, 4 pages.
International Search Report for application No. PCT/CN2012/070330, dated Oct. 18, 2012 (9 pages).

* cited by examiner

*Primary Examiner* — Jim Ketter
(74) *Attorney, Agent, or Firm* — Hamre, Schumann, Mueller & Larson, P.C.

(57) ABSTRACT

Disclosed are standardized reference genes for microRNAs and the use thereof. The reference gene is microRNA let-7d, let-7g, let-7i or a combination thereof. The reference genes have extremely high stability and accuracy compared to the currently most commonly used reference genes in microRNA quantitation.

11 Claims, 8 Drawing Sheets

INTERNAL REFERENCE GENES FOR MICRORNAS NORMALIZATION AND USES THEREOF

TECHNICAL FIELD

The present invention relates to the biotechnology and in particular, the internal reference genes for the miRNAs normalization and use thereof.

BACKGROUND

MicroRNAs (miRNAs) are a group of non-coding RNA molecules with approximate 22 nucleotides in length and play an important role in the network of gene regulation. In body fluid, such as serum, plasma, saliva, urine and milk, etc., miRNAs exist highly stably outside of the cells. MiRNAs are associated to many diseases. The abnormal expressions of miRNAs, especially of circulating miRNAs have been detected under many pathological conditions. These pathological conditions include cancers, diabetes, heart failure, acute myocardial infarction and tissue damage, etc. Under certain pathological circumstances, in particular, with diseases such as cancers, the expression profile of miRNAs, especially the circulating miRNAs may significantly change according to the changes in physiological and pathological conditions. These researches have shown that miRNAs have great potential as non-invasive markers for molecular diagnosis and prognosis.

In recent years there have been several methods used for quantitative measurement of the miRNAs in clinical samples, such as Solexa sequencing, qRT-PCR and microarrays. The accuracy of the above-mentioned methods depends to a great extent on the reference gene(s) used. The reference gene(s) can be one gene or a combination of genes and shall be expressed stably under various experimental conditions and in different sample sets. In clinical application, detection of the miRNAs as biological markers must be normalized so that the detection process can be repeated in any lab. However, when quantitatively measuring the miRNAs, the changes of the amount of raw materials, the differences in sample collection and storage, and the efficiency differences in RNA extraction and enzymolysis may all lead to potential deviation and errors in quantification. In small size samples, the amount of total RNA is even smaller than the limits of the precise quantification by spectrophotometric method. All of the above-mentioned factors severely reduced the accuracy and reliability in quantitative analysis of miRNAs.

An ideal reference gene for miRNA normalization should meet the following requirements:

1) it is expressed stably in all samples and under all experimental conditions;

2) the amount of its expression can be compared to the study subjects;

3) it possesses the similar attributes of the study subjects, such as the stability and size of RNA, etc.

So far when the sample miRNAs are standardly measured, the selection of the reference gene relies still on experience, and the reference gene that meets the above-mentioned requirements has not been defined. In recent years artificially synthesized non-human (such as nematode) miRNAs have been used as exogenous control for normalized miRNAs detection. However, the exogenous controls are not the first choice because they can not correct the discrepancy in sample collection. Therefore, it is not an ideal reference gene.

Meanwhile, some endogenous genes have been frequently used as internal reference genes for the detection of tissue/cell miRNAs, such as 5SrRNA, 18SrRNA and U6 etc. Yet due to the fact that these genes are not miRNAs, they cannot represent the composition of miRNAs; and the efficiency of extraction, reverse transcription and PCR amplification of these genes might be different from that of the miRNAs. Therefore these genes are not the ideal choice, either.

Till present no research has been conducted on systematic characterization and evaluation on ideal reference gene(s) for miRNA normalization. Therefore, in this field it is necessary to develop the reference gene(s) for microRNA normalization and to establish an efficient normalization plan for the detection of miRNAs, especially circulating miRNAs.

DESCRIPTION

The object of the present invention is to provide an internal reference gene(s) for miRNAs normalization and the use thereof.

Another object of the present invention is to provide a method to screen the kind of internal reference gene(s) and the use thereof.

In the first aspect, the present invention provides the use of miRNAs or the corresponding nucleic acid sequences or complementary sequences thereof as the internal reference genes for miRNA normalization, in which said miRNAs are selected from the following group: let-7d, let-7g, let-7i, or the combinations thereof.

In the second aspect, the present invention provides an internal reference gene set for miRNA normalization, in which said internal reference gene set includes the combination of the two or three of miRNAs selected from the following group: let-7d, let-7g and let-7i.

In another preferred example, said internal reference gene set consists of 3 miRNAs, let-7d, let-7g and let-7i, or said internal reference gene set comprises at least 3 miRNAs said above.

In another preferred example, said internal reference gene set also includes one or more of auxiliary internal reference genes selected from the following group: U6, RNU44, RNU48, miR-16, miR-191, miR-103, miR-23a, GADPH, β-actin or the combinations thereof.

In the third aspect of the present invention, a method for the quantification of miRNAs through normalization is provided, including the steps:

(1) determining the absolute concentration of the miRNAs to be tested in a sample;

(2) comparing the absolute concentration of miRNAs to be tested obtained from step (1) to that of the internal reference gene in the sample, thereby obtaining the relative concentration of the miRNAs to be tested.

In another preferred example, said internal reference genes in step (2) are selected from the following group: let-7d, let-7g, let-7i or the combinations thereof.

In another preferred example, said internal reference gene set is selected from the combinations of the following three miRNAs: let-7d, let-7g, and let-7i.

In another preferred example, in step (2), the absolute concentration of miRNAs to be tested is compared with the total concentration of let-7d, let-7g and let-7i in the sample.

In another preferred example, said sample is selected from the following group: blood, plasma, serum, body fluid, cells, tissues, organs or the combinations thereof.

In another preferred example, said sample is from the normal individuals or ill individuals.

In another preferred example, said sample to be tested is from human or non-human mammals, preferably from human.

In another preferred example, said internal reference genes also include one or more of auxiliary internal reference genes selected from the following group: U6, RNU44, RNU48, miR-16, miR-191, miR-103, miR-23a, GADPH, β-actin or the combinations thereof.

In the fourth aspect of the present invention, a biochip for quantitatively detecting miRNAs is provided, said chip including solid phase carrier and detection spots on said solid phase carrier and said detection spots are used for specifically detecting miRNAs or the corresponding nucleic acid sequences or complementary sequences thereof according to the first aspect of the present invention, or used for detecting the internal reference gene set according to the second aspect of the present invention.

In the fifth aspect of the present invention, a kit for the detection of miRNA is provided, said kit including a container and the reagent for detecting the internal reference gene or the internal reference gene set, or the chip according to the fourth aspect of the present invention in said container, wherein said internal reference gene or internal reference gene set includes one, two or three of the following miRNAs: let-7d, let-7g and let-7i;

wherein, said reagent is selected from the following group:

(a) primers or pairs of the primers for specifically amplifying said internal reference gene(s);

(b) probes specifically hybridizing with the nucleic acid molecules of said internal reference genes;

wherein, said chip is a nucleic acid chip and said chip has detection spots for specifically detecting the nucleic acid molecules of said internal reference genes.

In another preferred example, said internal reference gene set includes let-7d, let-7g and let-7i.

In the sixth aspect of the present invention, a method for screening internal reference genes for miRNA normalization is provided, including the following steps:

(1) obtaining the disease and the normal samples, and extracting as well as quantifying the RNA in the samples;

(2) sequencing the miRNAs from the samples obtained in step (1) to obtain the sequences of the miRNAs from the samples;

(3) analyzing the stability of the miRNAs, and selecting the miRNAs with stability higher than the average level as candidate genes.

In another preferred example, said method also includes step (4): verifying the candidate genes obtained in the step (3).

In another preferred example, said verification in step (4) includes the steps:

(i) comparing the stability of the control internal reference genes with the candidate genes obtained in step (3) by using qRT-PCR;

(ii) evaluating the control internal reference genes and the candidate genes by using geNorm and NormFinder algorithms.

In another preferred example, following step (4), step (5) is included: determining the stability and accuracy of the candidate genes under extreme conditions.

In another preferred example, said extreme conditions are selected from the following group: in the presence of ribonuclease, under the circumstances of acidic condition, basic condition or the combinations thereof.

In another preferred example, said sequencing in step (2) includes the steps:

Hybridizing the miRNAs obtained from the samples with the fixed sequencing probes on the solid phase carrier, performing solid phase bridge PCR amplification to form the sequencing cluster; then sequencing the sequencing cluster using sequencing by synthesis to obtain the sequences of the miRNAs from the samples.

In another preferred example, said analysis in step (3) includes: analyzing the stability of the miRNAs by using geNorm and MormFinder algorithms to select the genes with minimal square deviation as the candidate genes.

It should be understood that, within the scope of the present invention, each of the above-mentioned technical features and each of the technical features described infra (such as in the Examples) can be combined thereby creating novel or preferred technical solutions. To confine the length of description, such possible novel or preferred technical solutions are not described individually hereby.

BRIEF DESCRIPTION OF THE DRAWINGS

The following figures are used for illustrating the embodiments of the present invention, while not to limit the scope of the invention as defined by the claims.

FIG. 2 demonstrates the results obtained from screening the stable reference genes by using Solexa sequencing, wherein FIG. 2A demonstrates the results obtained from determining the level of the miRNAs by using Solexa sequencing, FIG. 2B demonstrates the mean value (Solexa readout±standard deviation) of the expression of the selected miRNAs, FIG. 2C demonstrates the results for selecting the most stable reference genes among 25 genes by using geNorm, FIG. 2D demonstrates the results for determining the optimal amount of the reference genes for accurate normalization by using geNorm, FIG. 2E demonstrates the results for screening the most stable reference genes or reference gene combinations by using geNorm, and FIG. 2F demonstrates the results for determining the most stable reference genes by using NormFinder.

FIG. 3 demonstrates the results obtained from verifying the stability of the selected candidate genes by using real-time fluorescence quota PCR, wherein

THE MODES FOR CARRYING OUT THE INVENTION

The inventors of the present application have, through extensive and in-depth research, normalized circulating miRNAs in healthy individuals and patients with various diseases, for the first time found out that, among numerous miRNAs, any one of the three genes let-7d, let-7g, let-7i or their combinations can all be used as internal reference gene(s) for detecting the miRNAs, and feature extremely high stability and accuracy. Basing on such findings, the present invention was accomplished.

In particular, by using high throughput Solexa sequencing method, the inventor detected the expression levels of the serum miRNAs in the samples from the healthy individual control group and the patients; and then applying geNorm and NormFinder algorithms, the inventors analyzed the sequencing data and obtained the best candidate reference genes; using quantitative reverse transcription PCR (qRT-PCR) to verify, the inventors detected best candidate reference genes and commonly used reference genes (U6, RNU4 and RNU48 etc.) in large samples of healthy individual controls and patients with various diseases, and found out that, in the healthy individual control group and patients with various diseases, let-7d, let-7g and let-7i or the combinations thereof all can be used as internal reference genes.

miRNAs and Circulating miRNAs miRNAs are a group of non-coding single-stranded ribonucleic acid molecules with approximate 19-23 nucleic acids. They are highly conserved in evolution and widespread in animal and plant cells. MiRNAs play an important role in regulating gene expression levels, and the diversity of their sequences, structures, abundance and expressions enable them to be powerful regulatory factors for messenger RNAs. The discovery of miRNAs has broaden the horizon of understanding the control on protein synthesis, supplemented a new method to more rapidly and efficiently regulate molecules at the RNA level, and thus demonstrated a network of all-directional and multi-level in regulating gene expression in the cells.

Even in the presence of certain RNases, some miRNAs circulate in the body fluid with high concentration and intact structure. These miRNAs are therefore called circulating miRNAs. The high stability of the circulating miRNAs may be due to: 1. circulating miRNAs protected through being wrapped by microvesicle; 2. circulating miRNAs binding with proteins (such as Argonaute 2, high density lipoprotein and nuclear phosphoprotein 1). Through extensive and in-depth research, the inventors have found that, among numerous endogenous miRNAs, let-7d, let-7g, let-7i or the combinations thereof can all be used as internal reference genes for detecting miRNAs.

The nucleic acid sequences of let-7d, let-7g, let-7i are shown in Table 1.

TABLE 1

| microRNA | Nucleic acid sequence | SEQ ID NO. |
| --- | --- | --- |
| Let-7d | AGAGGUAGUAGGUUGCAUAGUU | 1 |
| Let-7g | UGAGGUAGUAGUUUGUACAGUU | 2 |
| Let-7i | UGAGGUAGUAGUUUGUGCUGUU | 3 |

The Advantage of the Reference Gene Combinations Over One Single Reference Gene

Normalization usually uses single reference gene, such as GAPDH, α-tubulin and β-actin, etc., however, the expression of such gene varies significantly under different conditions, and using single gene for normalization may lead to remarkable errors in quantitative analysis of transcription. The invention provides a strategy using multiple reference genes for normalization, the combination of let-7d, let-7g and let-7i was determined as the best gene combination for normalization through calculation, and using the combination of three miRNAs was more reliable for normalization than using the combination of two miRNAs or single miRNA.

High Throughput Sequencing

An ordinary person skilled in the art usually uses three models of second generation sequencing platforms for high throughput sequencing: 454 FLX (Roche), Solexa Genome Analyzer (Illumina) and SOLID (Applied Biosystems). Compared with traditional 96-channel capillary tubes for sequencing, the common feature of these platforms is extremely high sequencing-throughput. One experiment of high throughput sequencing can obtain 0.4-4 million sequences and 25 bp-450 bp length depending on different platforms. Therefore, from 1G up to 14G base number could be obtained in one sequencing experiment using different platforms.

Solexa high throughput sequencing includes two steps of DNA cluster formation and machine loading sequencing: hybridizing the mixture of products from PCR amplification with the sequencing probes fixed on the solid phase carrier and performing solid phase bridge PCR amplification, thereby forming the sequence cluster; sequencing said sequence cluster by using "sequencing by synthesis".

The DNA clusters are formed through such reactions: the sequencing chip (flow cell) with a layer of single stranded primers on surface is used, a single stranded DNA fragment is fixed on the chip surface through the complementary base pairing between the adapter sequence and the primer on the chip surface; through amplification the fixed single stranded DNA becomes double stranded DNA, and then single stranded DNA again, of which one end is mounted on the sequencing chip, and the other end randomly complemented with another primer nearby thus being mounted to form a "bridge"; millions of DNA single molecules are having the above-mentioned reaction simultaneously on the sequencing chip; the single stranded bridges formed use the primers around for amplification and amplify again on the surface of amplification chip, forming double strands, the double strands become single strand, forming the bridges once again, which will be the templates for the next round of amplification. After 30 rounds of amplification, every single molecule has been amplified 1000 times thus became monoclonal DNA clusters.

DNA clusters are sequenced on a Solexa sequencer through "Sequencing on Synthesis". In the sequencing reaction, the four bases are labeled with different fluorescence, and each base terminus is sealed by a protecting base. Only one base is allowed to be added in a single reaction. The protecting group is removed after scanning and obtaining the color readout in the reaction, and then the next reaction continues in the same way. The accurate sequences of the bases are obtained after the reaction cycles as mentioned above. The samples are differentiated with Index during the Solexa Multiplexed Sequencing. After routine sequencing, seven additional sequencing cycles are performed for the Index parts, and twelve different samples can be distinguished in one sequencing channel through identifying the Index.

Method for Screening the Normalization Internal Reference Genes

Figure 1:
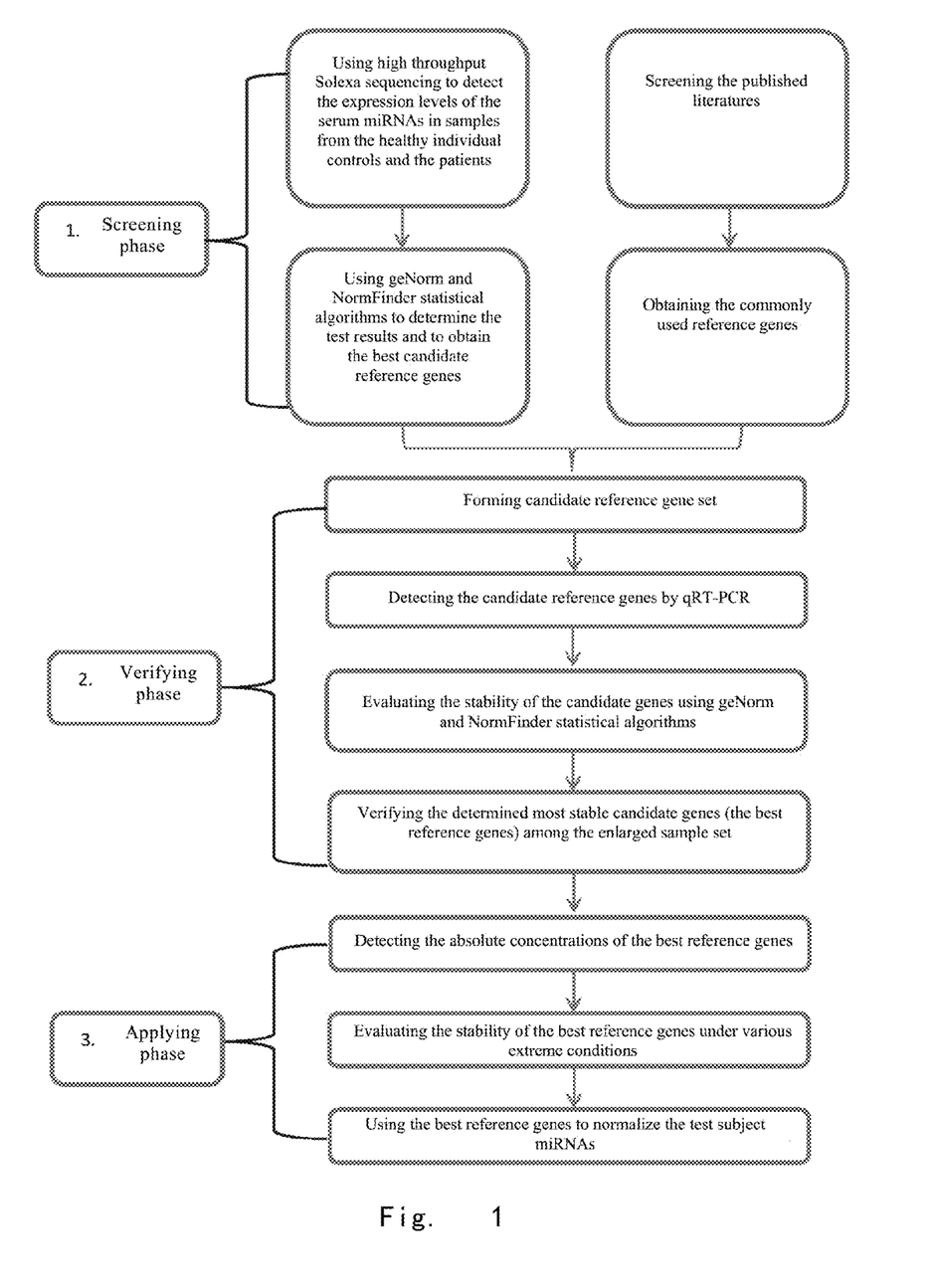
FIG. 1 demonstrates the process of screening the best reference genes for miRNA detection in a preferred embodiment of the present invention.

In order to provide the appropriate normalization reference genes for circulating miRNAs, the invention also provides a screening strategy (see FIG. 1). In a preferred example, the screening strategy includes three main steps:

The first step: screening the sample set which represents the broad physiological and pathological conditions by using Solexa sequencing, and sorting the genes according to the stability by using geNorm NormFinder statistical algorisms thus selecting the most stable candidate genes indicated with the minimal square errors in different samples. Meanwhile, the commonly used reference genes are determined by screening the literatures; The second step: forming the best candidate reference gene set by combining the results from the above-mentioned two aspects, said best candidate genes are detected By using qRT-PCR, and the stability of the candidate genes is evaluated by using geNorm and NormFinder statistical algorisms. Consequently, among the larger sample set, the most stable candidate genes, i.e. the best reference genes are further identified and verified;

The third step: by using said best reference genes, detecting the absolute concentrations of said best reference genes and evaluating the stability of the best reference genes under various extreme conditions, and normalizing the tested target miRNAs by using the best reference genes.

Method of Detection

The invention also provides a method of quantitative normalization of miRNAs which includes the following steps:

(1) determining the absolute concentration of the miRNAs to be tested in the samples;

(2) comparing the absolute concentrations of the miRNAs to be tested obtained from step (1) with that of the internal reference genes in the samples to obtain the relative concentrations of the miRNAs to be tested.

In one preferred example of the invention, said internal reference genes in step (2) are selected from the following group: let-7d, let-7g, let-7i or the combinations thereof; preferably, comparing the absolute concentrations of the miRNAs to be tested with the concentration of let-7d, let-7g and let-7i in the sample.

In another preferred example, said samples to be tested includes: serum, plasma, blood, urine, milk, cells, tissues, organs or the combinations thereof.

In another preferred example, said samples to be tested are from the normal individuals and ill individuals. Said samples to be tested are from human or non-human mammals, preferably from human.

In the present invention, there is no particular restriction on the method of detecting the miRNAs, and representative examples include (but not limited to): RT-PCR, real-time PCR, Northern Blot, Solexa sequencing, in-situ hybridization (ISH), rolling cycle amplification (RCA), Solexa sequencing or biochips.

Chips

The invention also provides a biochip for the detection of the miRNAs, said biochip including solid phase carrier and the detection spots on said solid phase carrier, and said detection spots are used for specifically detecting the miRNAs (let-7d, let-7g, let-7i, or the combinations thereof) or the corresponding nucleic acid sequences or complementary sequences thereof, or used for detecting the internal reference gene set consisting of the miRNAs.

The chip comprises the following components:

Solid phase carrier (such as substrates or microspheres) and oligonucleotide probes orderly fixed on the solid phase carrier.

The detecting chips in the present invention may include one or more, preferably more than ≥5, more preferably more than ≥10, most preferably ≥20 detecting spots.

Said solid phase carrier may be made of various materials commonly used in gene chips, such as but not limited to nylon membrane, reactive group (such as aldehyde-group and amino-group, etc.) modified slides or silicon wafers, unmodified slides and plastic substrates, etc. Said oligonucleotide probes are biotinylatized or fluorescence labeled probes.

Said miRNA chips can be prepared by the routine preparation methods for biochips known in the art. For example, if modified slides or silicon wafers are used as the solid phase carrier and the probes include amino-group modified poly-dT strings at their 5' ends, the oligonucleotide probes can be formulated into solution, then spotted onto the modified slides or silicon wafers by spotting robot and arranged into predetermined sequences or arrays, and placed overnight, thereby obtaining the miRNA chips of the present invention.

Kit

The invention also provides a kit, said kit includes reagents or chips for the detection of the internal reference genes or internal reference gene set, and said internal reference genes or internal reference gene set comprises one, two or three of the following miRNAs: let-7d, let-7g, and let-7i;

wherein, said reagent is selected from the following group:

(a) primes or pairs of primers for specifically amplifying said internal reference genes;

(b) probes specifically hybridizing with the nucleic acid molecules of said internal reference genes;

wherein, said chip is a nucleic acid chip and said chip has detection spots for specifically detecting the nucleic acid molecules of said internal reference genes. In another preferred example, said internal reference gene set includes let-7d, let-7g and let-7i.

Advantages of the Present Invention (1) The accuracy of the miRNAs normalization process is significantly improved by the selected internal reference gene;

(2) The internal reference genes in the invention are applicable to various experiment conditions;

(3) The stability of the internal reference genes according to the present invention is very high and can be used under extreme conditions.

The present invention will be further elaborated below with reference to specific examples. It should be understood that these examples are not to limit the scope of the present invention, rather to illustrate it. The methods of the experiments without indicated conditions in the following examples are generally performed under conventional conditions, such as those described in Sambrook et al., Molecular Cloning: A Laboratory Manuel (New York: Cold Spring Harbor Laboratory Press, 1989) or according to manufacturers' instructions.

General Methods

Extracting RNA from Serum Samples

The venous blood samples (about 5 ml each) collected from each donator are put in the serum separation tubes. The samples should be treated within 1 hour. After centrifuged at 800 g for 10 minutes at room temperature, the samples are centrifuged at 10,000 g for 15 minutes at room temperature to thoroughly remove the cell debris. The supernatants are collected and stored at −80° C. for analysis.

Several samples (5 mL each) are mixed to establish the serum strains, stirred vigorously, and then RNA is extracted from 50 mL serum mixture by TRIzol reagent (Invitrogen, Carlsbad, Calif., USA)

Real-time quantitative PCR detection and analysis: Total RNA is extracted from the 100 μL serum by one step purification using phenol/chloroform. Specifically, 300 μL water without RNase, 200 μL phenol and 200 μL chloroform are added sequentially into the 100 μL serum. The mixture is stirred vigorously and incubated for 15 minutes at the room temperature. After the layers separated, the aqueous layer is mixed with 1.5 fold volume of isopropanol and 0.1 fold volume of 3 mol/L of sodium acetate (pH 5.3). The mixture is stored at −20° C. for 1 hour and centrifuged at 16,000 g under 4° C. to obtain the RNA precipitate. The RNA precipitate is washed once by 75% ethanol and placed at the room temperature to dryness. Finally the RNA precipitate is dissolved in water without RNase and stored under −80° C. for the following analysis.

2. Analysis of the Circulating miRNAs by Solexa Sequencing

Small RNA molecules less than 30 bp are purified through PAGE, ligated at 5' end and 3' end thereof to one pair of Solexa adaptors, and fragments with approximate 90 bp (small RNA+adaptor) are separated from the gel after amplified for 17 cycles using adaptor primers. The purified RNA can directly be used for creating sequencing clusters. The sequence is analyzed using Illumina Genome Analyzer under the instructions given by the manufacturer. The Image files created from the sequencer are processed into digital data.

The subsequent proceeding includes: collecting the created data, evaluating the quality and depth of sequencing, calculating the length distribution of the small RNA and filtering the pollution readout. After shielding binding sequence, referring miRBase database 16.0 based on Smith-Waterman algorithm, clean readout is aligned. Only those candidate genes having the same sequences and length as the referring miRNA genes are marked as matching type. Finally, the total sequencing frequency of each sample may be debugged to 1 million at the same scale.

3. Quantitatively Determination of the Circulating miRNAs by Real-Time Fluorescence Quantitative PCR The circulating miRNAs are quantitatively determined by using Taqman miRNA PCR kit (Biosystems, Calif., USA). In particular, 5 μL of total RNA is reversely transcribed into cDNA by using the AMV reverse transcriptase (TaKaRa, DaLian, China) and the stem-loop RT primers (Applied Biosystems). Real time PCR is performed by using TaqMan miRNA probes (Applied Biosystems) and Biosystems 7300 Sequence Detection System (Applied Biosystems). All the reactions, including the control groups without the samples, are repeated for three times. After all the reactions are finished, $C_T$ value is set by using fixed threshold.

4. Analysis of the Stability of Genes

The stability of the candidate gene expression is calculated by using geNorm and NormFinder softwares. Solexa readout can directly be used for calculating the stability, and the $C_T$ value is converted into relative number using the method of $2^{-\Delta\Delta C_T}$.

geNrom software is used to sort the detected genes through stability value of expression (M value) thereof to determine the combinations of the two most stable reference genes or more stable genes for normalization. M value represents the average difference in comparison between the candidate genes and other genes in the same experimental group. The gene with the lowest M value is considered the most stable. By gradually excluding the genes with the highest M value, the stability of each candidate gene is sorted. The stability of the remaining genes is recalculated until the two most stable genes are found. Moreover, for geNorm program, it is required to calculate the differences in value ($V_n/V_{n+1}$) between the two normalization factors ($NF_n$ and $NF_{n+1}$) for the sequence to determine the best number of reference genes. Greater value in difference (>0.15) meant that one more reference gene needed to be added when calculating more reliable normalization factors. If the value in difference $V_n/V_{n+1}$ is lower than the suggested threshold value 0.15, then there is not necessary to add reference gene.

NormFinder is a method based on the model by which the stability of candidate reference gene expressions is determined by the differences in expressions between the groups (such as tumor group and normal group) and within the group. The main goal of this method is to determine the differences between the groups and within the group and to incorporate the two results into the stability value of the investigated genes. According to this algorithm, the gene with the lowest stability will be sorted to the forefront. In this study, two groups of sample with different types (the disease and the control) are analyzed by using NormFinder.

Example 1

Screening the Most Stable Reference Genes by Solexa Sequencing and Statistical Analysis In this example, database was first developed and then screened to determine the stable circulating miRNAs under various physiological and pathological conditions.

Among 23 samples analyzed, those meeting the following requirements were considered as the stable ones:
(1) expressed in all samples;
(2) higher expression compared with the average detection value;
(3) determining the stability in their expressions by measuring the standard deviation.

According to these above-mentioned criteria, 25 miRNAs were screened as candidate reference genes and the results were shown in FIG. 2.

Figure 2A:
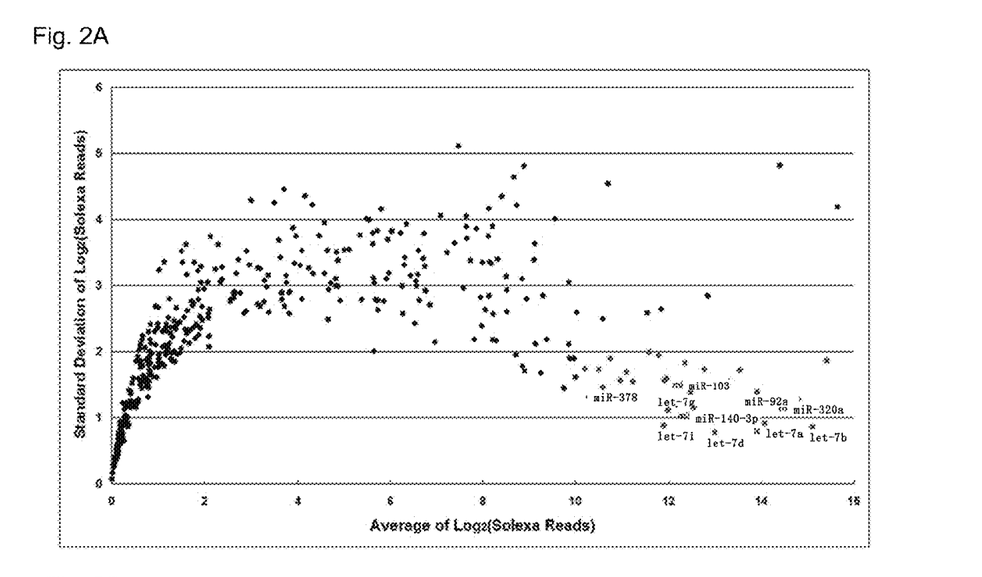
Figure 2B:
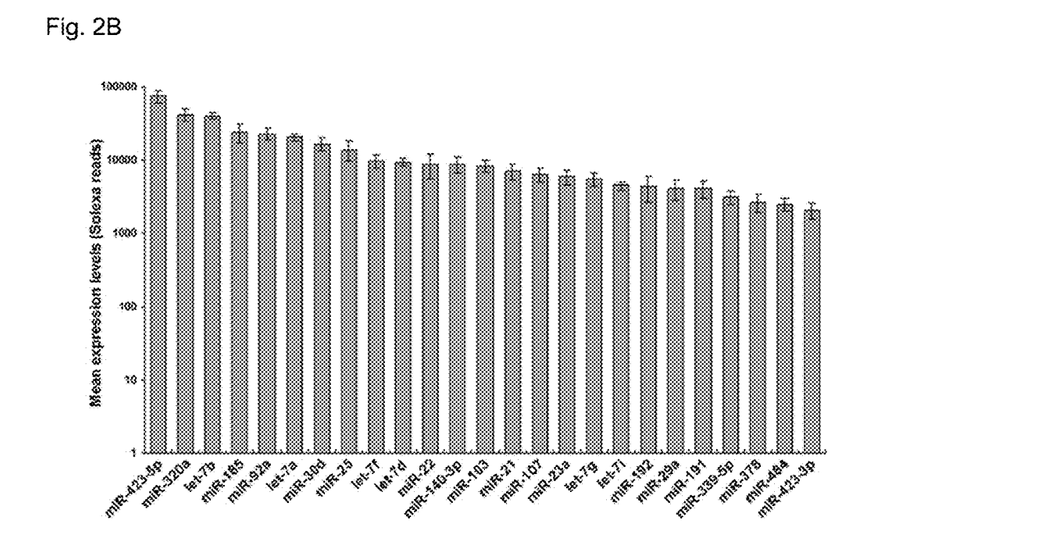
Figure 2C:
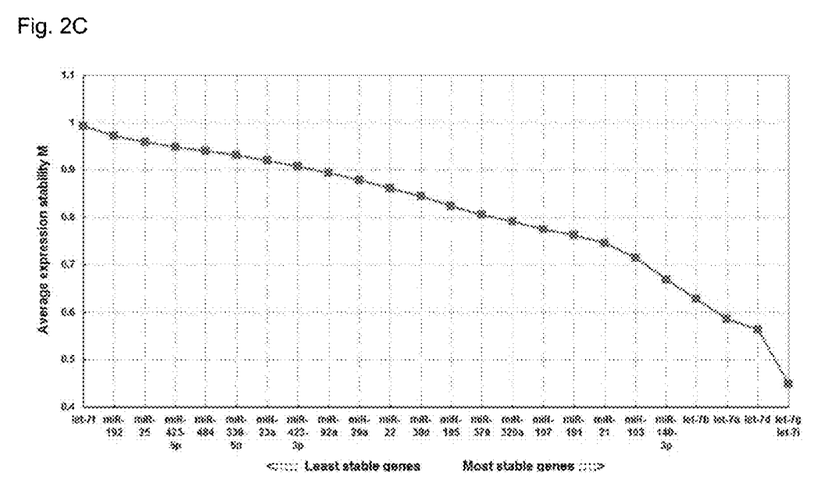

As shown in FIG. 2A, Solexa readouts were converted into logarithm and genes were sorted by their average expression levels and standard deviations. In all miRNAs screened out, 25 miRNAs exhibited higher abundance ($\log_2$-converted readout>10) and lower standard deviation (<1). The average expression values of the selected 25 miRNAs were shown in FIG. 2B.

The stability of the candidate reference genes was further evaluated by using two different methods (geNorm and NormFinder). The average expression stability value (M value) of a gene was calculated by using geNorm method through pairwise comparisons and the presumed reference genes were sorted based on the similarity of sample set expression profile. The average expression stability values of the 25 candidate reference genes were shown as curve in FIG. 2C. This curve was developed by excluding the unstable candidate reference genes through gradual regression, wherein let-7g was the most stably expressed gene in this group, let-7i and let-7d the next.

Analysis by geNorm algorithm can also be used to evaluate the stability value of the reference genes required for reliable and accurate normalization. Said algorithm adopted a measurement called V to determine the best numerical value of the reference genes, wherein the two normalization factors ($NF_n/NF_{n+1}$) for the sequence varies in pairwise ($V_n/V_{n+1}$). Cut-off value of 0.15 was considered as critical value and no more reference gene was added when V value was below 0.15.

Figure 2D:
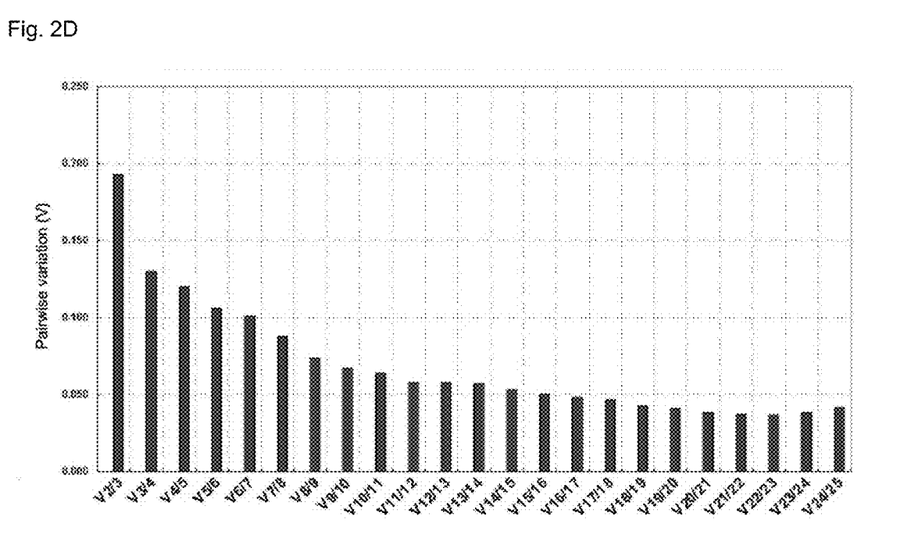
Figure 2E:
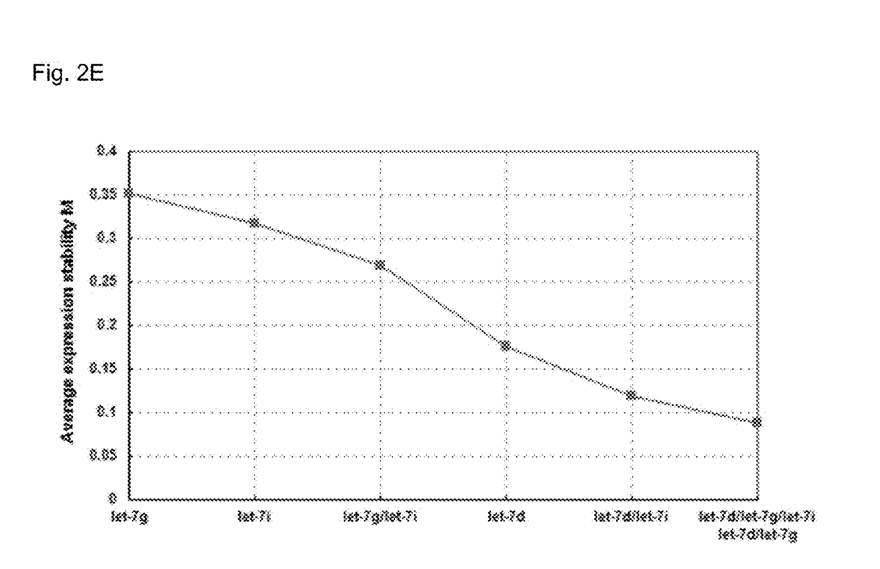

Results have shown that the combinations of let-7d, let-7g and let-7i were sufficient to accurately specify the target genes in data set, thereby creating the V value of 0.13 which was below the critical value of 0.15 (FIG. 2D). The combination of three miRNAs (let-7d+let-7g+let-7i) was statistically better than the two miRNAs (let-7d+let-7g, let-7d+let-7i or let-7g+let-7i) or a single gene from let-7d, let-7g or let-7i (FIG. 2E).

Figure 2F:
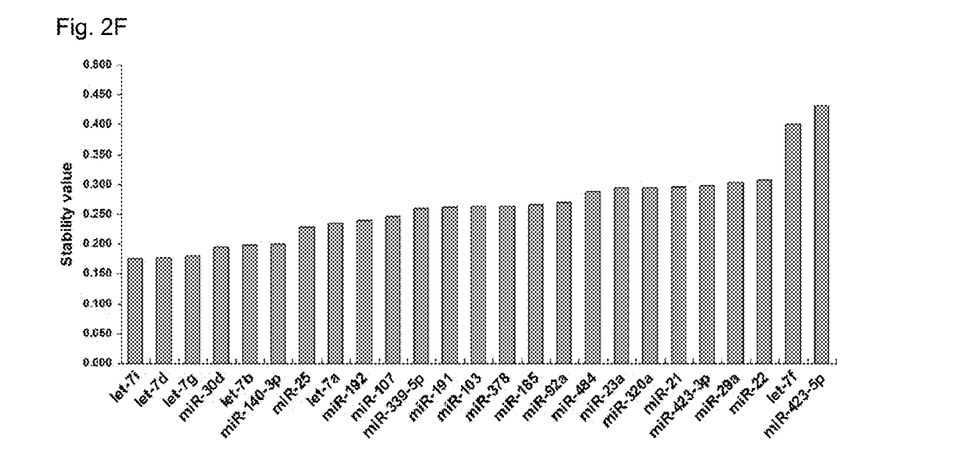

Additionally, by adopting the fixed statistical frame, NormFinder algorithm not only can evaluate the overall changes in expression of the candidate reference genes but also analyze the differences between groups (such as the tumor group and the normal group). NormFinder software separately evaluates the stability of the gene expression and the result obtained was basically the same as that determined by geNorm algorithm. NormFinder algorithm selected let-7i as the best reference gene for normalization, let-7d and let-7g the next (FIG. 2F).

Example 2

Screening Other Candidate Reference Genes

In this example, three candidate reference genes selected in the previous example were further evaluated and analyzed together with some commonly used reference genes, including big molecule RNA (GAPDH and β-actin), small nuclear RNA/small nucleolar RNA (snRNA/snoRNA), (U6, RNU44 and RNU48) and housing keeper miRNA (miR-16, miR-191, miR-103 and miR-23a). The inventor selected GAPDH and β-actin based on the previous reports about the stability of their expressions in tissues or cells. U6, RNU44, RNU48, miR-16, miR-191, miR-103 and miR-23a were selected since they were commonly used as reference genes when tissue/cell miRNAs were detected. Additionally, U6 and miR-16 were paid particular attention due to the fact that they have been used as reference genes for the normalization of circulating miRNAs.

Example 3

Verifying the Stability of the Candidate Reference Genes

In this example, the expression profile of the candidate reference genes in the samples from the 21 cancer patients and the 35 healthy individual control group were further evaluated by using real time fluorescence quantitative PCR.

Firstly, let-7d, let-7g and let-7i in the serum were detected and the combination of let-7d, let-7g and let-7i was represented as "let-7d/let-7g/let-7i". miR-20a, miR-21, miR-24 and miR-25 were used as controls.

Figure 3A:
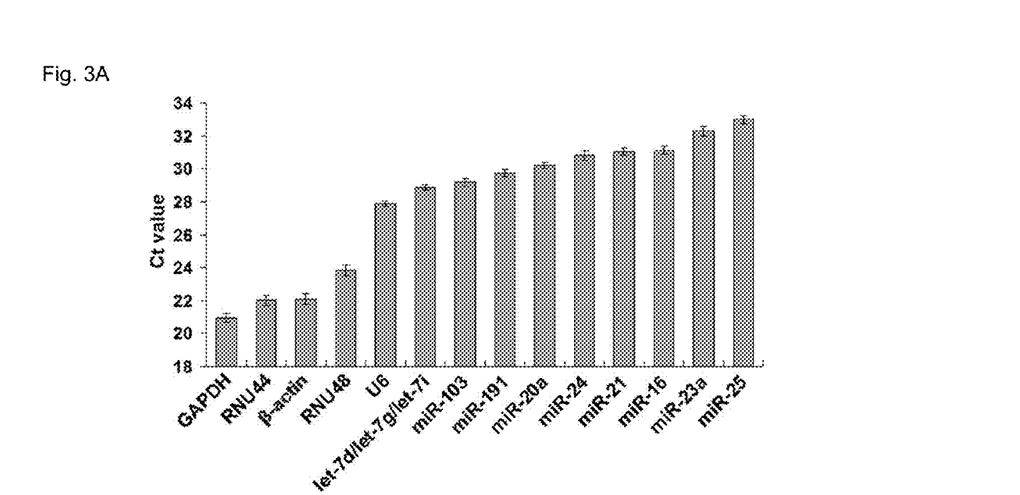
FIG. 3A shows the results of the expression levels of the candidate reference genes, FIG. 3B demonstrates the results for determining the optimal amount of the reference genes for accurate normalization by using geNorm, FIG. 3C demonstrates the results for determining the most stable reference genes by using NorFinder, and FIG. 3D demonstrates the results of the expression levels of the most preferred reference genes from vast serum samples.

Results have shown (FIG. 3) that the distribution range of the $C_T$ value of the reference genes was relatively broader which was between 20.9 and 33.0 and the expression of GAPDH was the highest (average $C_T \pm SE=20.9 \pm 0.27$), whereas the expression of miR-25 was the lowest (average $C_T \pm SE=33.0 \pm 0.23$). The deviation in expression of β-actin was the highest (SE=0.35) and that of the let-7d/let-7g/let-7i was the lowest (SE=0.15). The average readout and the range of the $C_T$ value of all reference genes were shown in FIG. 3A.

Figure 3B:
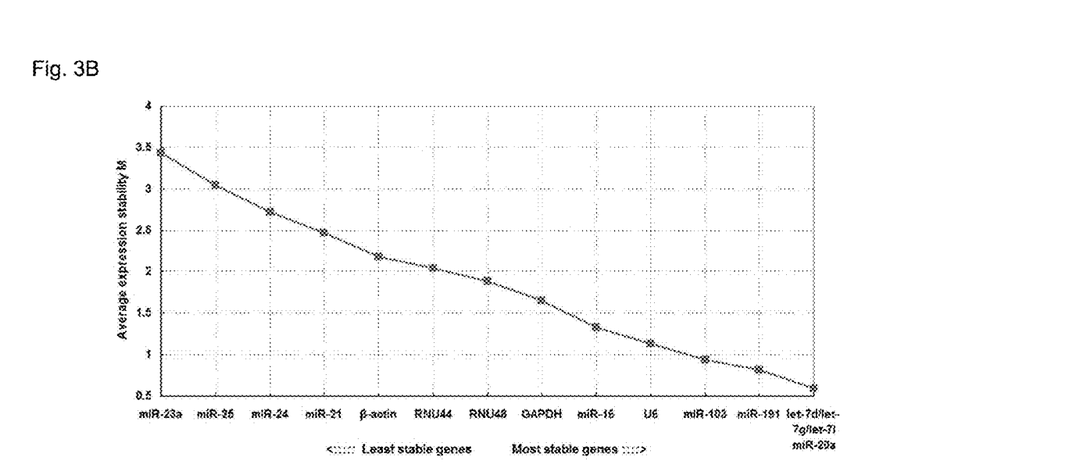

Then, the reference genes were sorted according to the stability of their expression by using geNorm and NormFinder algorithms. Based on geNorm algorithm, let-7d/let-7g/let-7i with the lowest stability value exhibited the most stable expression level thus being selected as the best reference gene (FIG. 3B). In contrast, miR-191, miR-103, U6, miR-16, RNU48 and RNU44 which are commonly used in real time fluorescence quantitative miRNA experiments, was below let-7d/let-7g/let-7i, which demonstrated that they could not be considered as reliable reference genes for normalizing the data. MiR-21, miR-24 and miR-25 were the lowest, behind all reference genes used in arrangement, which demonstrated that their expression profile in serum indeed reflected significant changes under the disease conditions.

Figure 3C:
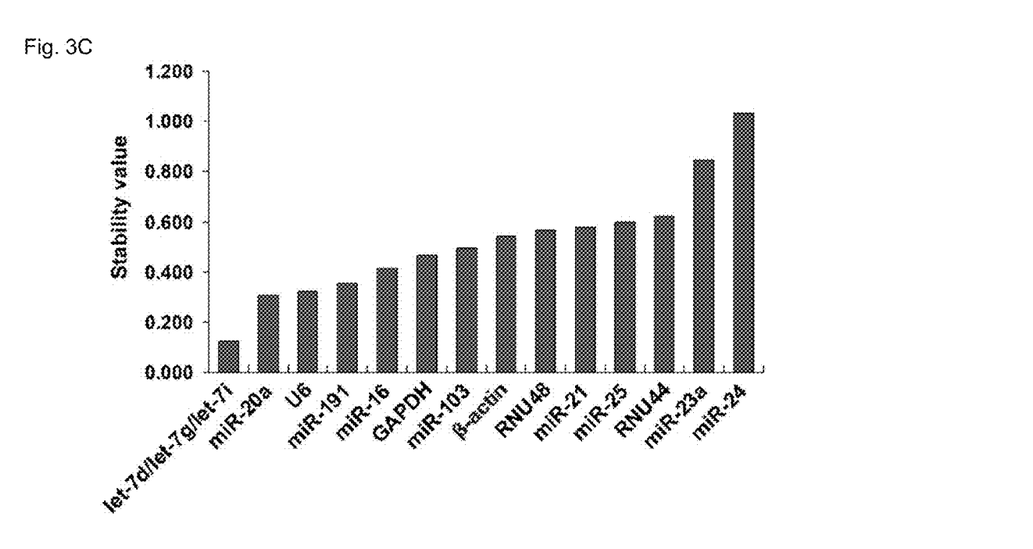

NormFinder algorithm confirmed the results from the geNorm algorithm which demonstrated that let-7d/let-7g/let-7i were the most reliable reference genes whereas miR-24 with the least stability (FIG. 3C).

Finally the selected best reference genes were further verified in a big sample set including 1278 healthy individual controls, 254 patients with cancers, 201 patients with inflammation and 320 patients with type II diabetes.

Figure 3D:
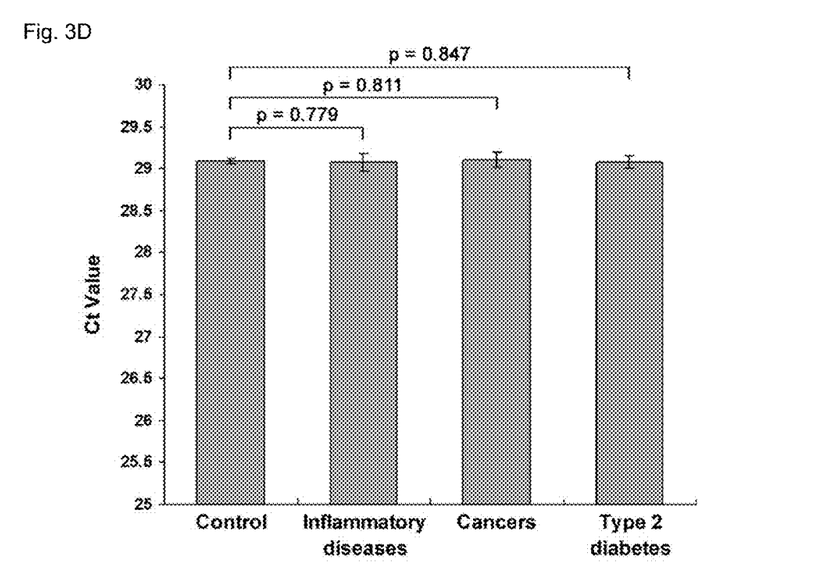

Results shown in FIG. 3D demonstrated that the expression level of the selected reference genes kept constant under the separate disease conditions and individual testing.

Example 4

The Characteristic of the Absolute Concentration of the Circulating let-7d/let-7g/let-7i in Serum In this example, the linear dynamical range and the sensitivity of let-7d/let-7g/let-7i were measured using qRT-PCR detection.

The synthesized single stranded let-7d/let-7g/let-7i was diluted continuously more than 10 orders of magnitude and detected by using qRT-PCR. The obtained $C_T$ values were plotted versus the corresponding input amount of the let-7d/let-7g/let-7i, thereby obtaining the standard curve.

Figure 4A:
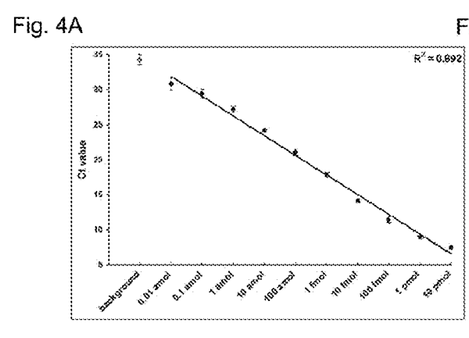

The decrease in the amount of let-7d/let-7g/let-7i resulted in the increase in average $C_T$ value with Pearson correlation coefficient R=0.992 (FIG. 4A). The result from the study has shown that, the change of let-7d/let-7g/let-7i that can be measured by using qRT-PCR is at least 10 orders of magnitude, and the amount of let-7d/let-7g/let-7i that can be detected in PCR reaction could be as little as 0.01 amol (corresponding to 6000 copies). Additionally, the characteristics of the expression level of let-7d/let-7g/let-7i in RNA samples extracted from various amount of serum have been studied by using qTR-PCR.

Figure 4B:
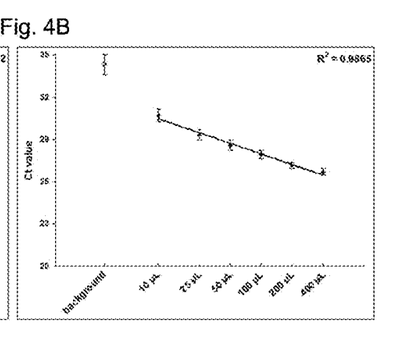
FIG. 4B demonstrates the results of the correlation between serum volume and the CT value (n=5)

The obtained $C_T$ values were plotted versus the amount of serum for RNA extraction, and there was a good linear correlation (R=0.9865) between the amount of serum and the $C_T$ values in qRT-PCR detection (FIG. 4B). The results from multiple samples have shown that let-7d/let-7g/let-7i could be efficiently detected and reliably compared in serum as little as 10 μL. Referring the standard curve, the absolute concentration of let-7d/let-7g/let-7i in serum was calculated as 271.35±21.48 fmol/L.

Example 5

The Stability of let-7d/let-7g/let-7i in Serum

As reference genes suitable for clinical trails, let-7d/let-7g/let-7i in serum should be stable during an appropriated time period, tolerant to severe conditions thus suitable for routine processing of clinical samples. Therefore, in this example, the stability of circulating let-7d/let-7g/let-7i was evaluated by using the processed serums from prolonged storage or under severe conditions, in which severe conditions included ribonuclease (RNase) degradation, extreme pH and freezing-thawing cycle, etc.

Figure 4C:
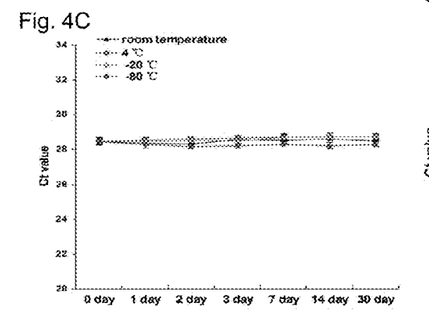
FIG. 4C demonstrates the results of the stabilities of let-7d/let-7g/let-7 (n=5) in serum after stored for extended time.
Figure 4D:
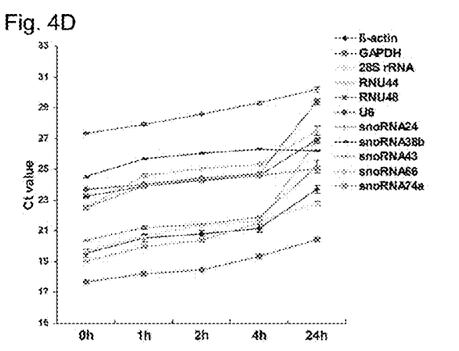
FIG. 4D demonstrates the results of the instabilities of other RNAs in serum (n=5), FIG. 4E demonstrates the results of the stabilities of let-7d/let-7g/let-7i in serum (n=5) after the degradation of ribonuclease, FIG. 4F demonstrates the results of the instabilities of other RNAs in serum (n=5) after the degradation of ribonuclease, and FIG. 4G and FIG. 4H demonstrate the results of stabilities of let-7d/let-7g/let-7i (n=5) under acidic and basic conditions, respectively.

Firstly, the stability of let-7d/let-7g/let-7i in serum stored under different temperatures (room temperature, 4° C., −20° C. or −80° C.) and for different time periods (1, 2, 3, 7, 14 or 30 days) was investigated. Results have shown that, when the storage time (long-term and short-term) or storage conditions (−0° C. and high temperatures) was different, there was no significant difference in $C_T$ value (FIG. 4C). In contrast, big molecule RNAs (β-actin, GAPDH and 28s rRNA) and snRNA/snoRNA (U6, RNU44, RNU48, snoRNA24, snoRNA38b, snoRNA43, snoRNA66 and snoRNA74a) were degraded rapidly within 24 hour if stored at room temperature (FIG. 4D). Therefore inherent RNase in serum caused the rapid degradation of big molecule RNAs and snRNA/snoRNA, yet had relatively less effect on circulating let-7d/let-7g/let-7i.

Figure 4E:
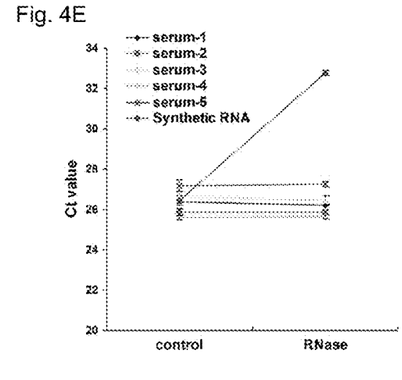
Figure 4F:
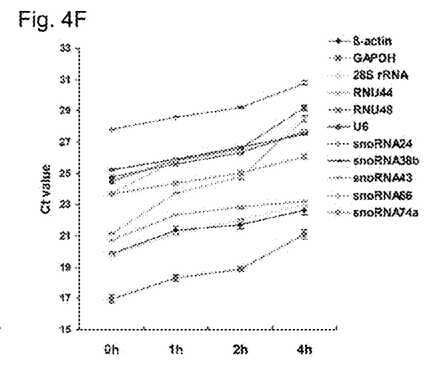
Figure 4G:
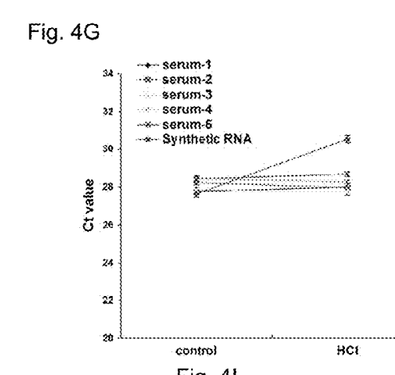
Figure 4H:
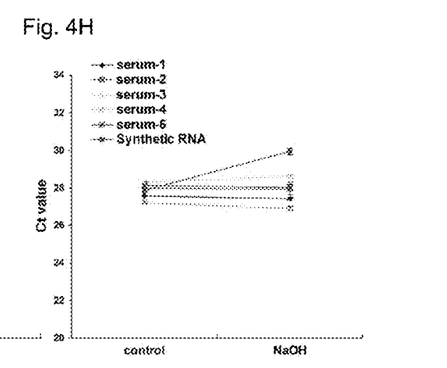

Secondly, after RNase was added into serum samples, circulating let-7d/let-7g/let-7i exhibited considerable tolerance to degradation by RNase whereas the synthesized let-7d/let-7g/let-7i was rapidly degraded (FIG. 4E). After processed by RNase, the concentration of the big molecule RNAs and snRNA/snoRNA in serum also degraded rapidly (FIG. 4F).

Figure 4I:
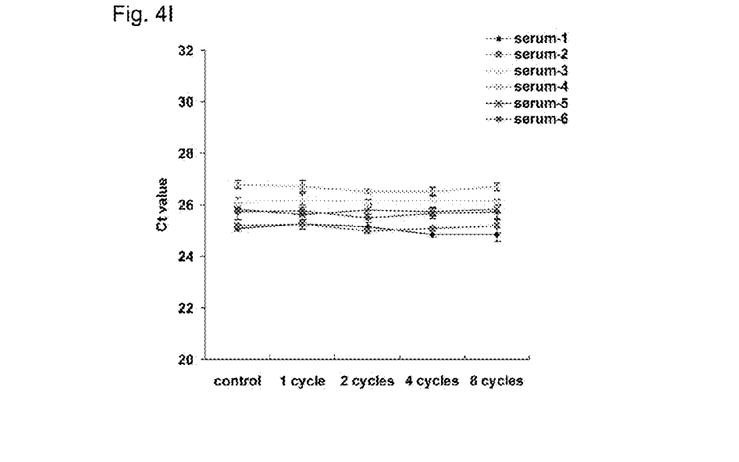
FIG. 4 demonstrates the features of absolute concentrations and stabilities of serum let-7d/let-7g/let-7i under various extreme conditions, wherein FIG. 4A demonstrates the results of the dynamic range and sensitivity of the let-7d/let-7g/let-7i (n=5) measured by using real-time fluorescence quota PCR.

Further, the stability of the serum miRNAs under the acidic condition (pH=2.0) or basic condition (pH 12.0) and the effects of freezing-thawing conditions on the expression level of serum let-7d/let-7g/let-7i were also investigated. Results have shown that the expression levels of let-7d/let-7g/let-7i in serum did not change substantially after incubated for 4 hour under the acidic or basic condition. Additionally, after repeatedly freezing and thawing for 8 cycles, the expression levels of let-7d/let-7g/let-7i in serum did not change obviously, either (FIG. 4I)

Summing up, the stability of the circulating let-7d/let-7g/let-7i was high, and storage for extended time, RNase treatment, acidic/basic condition and freeing-thawing had no significant effect on its stability.

Example 6

Significant Effect on the miRNA Quantitation by Different Normalization Methods In this example, the testing results of miRNAs normalization using the stable or instable reference genes were investigated.

It has already been shown that the circulating miR-25, miR-214, miR-223 and miR-483-5p were the up-regulated oncogenes in the serum of cancer patients, therefore these four genes were selected as target genes.

Using real time fluorescence quantitative PCR detection and $2^{-\Delta\Delta C_T}$ method, the relative expression levels of the above-mentioned miRNAs in the serum from the cancer patients and the healthy individual control were determined, and normalized to the serum volume, U6, miR-191 or the combination of let-7d, let-7g and let-7i, respectively, and only the miRNAs with average fold change >2 and P value <0.05 were considered as being significantly up-regulated.

Figure 5:
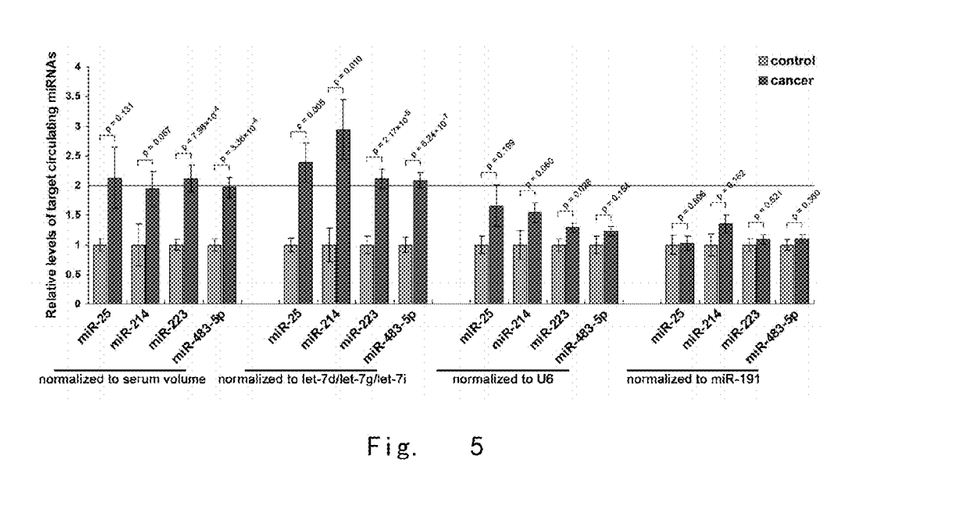
FIG. 5 demonstrates the effects of different methods of normalization on target circulating miRNAs.

Results have shown that methods of normalization indeed significantly effected the fold change (FIG. 5). In particular, upon normalization to the combination of let-7d, let-7g and let-7i (the most stable reference genes), serum miR-25, miR-214, miR-223 and miR-483-5p in cancer patients were significantly up-regulated compared with those in the normal control group. Upon normalization to serum volume, the trend in fold change was consistent with that upon the normalization to let-7d/let-7g/let-7i, but only the expression level of miR-223 in cancer patients was significantly increased. However, upon normalization to U6 (the most unstable reference gene), there was no significant difference between the expressions of serum miR-25, miR-214, miR-223 and miR-483-5p in cancer patients and those in the normal control group. Upon normalization to stable reference miRNAs, it showed that, the expressions of miR-25, miR-214, miR-223 and miR-483-5p in the cancer samples were up-regulated compared with those in non-malignant tumor control samples. In contrast, upon normalization to miR-191, there is no significant change in the expressions of the above-mentioned miRNAs.

Therefore using appropriate normalization gene would increase the sensitivity and reproducibility of the result whereas choosing the non optimal reference genes may lead to the inaccuracy of the result.

Example 7

Kit

In this example, a kit is provided. Said kit contains the reagent for the detection of the internal reference genes, and said internal reference genes include: microRNA let-7d, microRNA let-7g, and microRNA let-7i, wherein, said reagent was selected from the following group: (a) primers or pairs of the primers for specifically amplifying said internal reference genes; (b) probes specifically hybridizing with the nucleic acid molecules of said internal reference genes.

All the literatures mentioned in the present invention have been used as references so as each literature used as reference independently. Additionally, it should be understood that any ordinary person skilled in the art may alter or modify the present invention after having read the above-described content of the invention. Any of the equivalent forms will fall into the scope of the present invention defined by the claims.

The invention claimed is:

1. A probe for an internal reference gene set for microRNA normalization, wherein said internal reference gene set includes let-7d+let-7g, let-7d+let-7i or let-7d+let-7g+let-7i, the DNA probe is labeled with a report group or a fluorescence quenching group.

2. The probe according to claim 1, wherein said internal reference gene set includes the let-7d+let-7g+let-7i.

3. The probe set according to claim 1, wherein said internal reference gene set further includes one or more of auxiliary internal reference genes selected from the following group: U6, RNU44, RNU48, miR-16, miR-191, miR-103, miR-23a, GADPH, β-actin or a combination thereof.

4. A method for quantification of a miRNA through normalization, comprising:
   (1) determining absolute concentrations of the miRNA and an internal reference gene set in a sample;
   (2) comparing the absolute concentration of said miRNA with that of said internal reference gene set in the sample, thereby obtaining a relative concentration of the miRNA,
   wherein said internal reference gene set includes let-7d+let-7g, let-7d+let-7i, or let-7d+let-7g+let-7i.

5. The method according to claim 4, wherein in step (2), the absolute concentration of the miRNA is compared with a total concentration of let-7d, let-7g and let-7i in the sample.

6. The method according to claim 4, wherein said sample is selected from the following group: blood, plasma, serum, body fluid, cells, tissues, organs or a combination thereof.

7. A biochip for quantitatively detecting a miRNA, wherein said chip includes solid phase carrier and detection spots on said solid phase carrier, and said detection spots are used for specifically detecting the internal reference gene set of claim 1.

8. A kit used for the detection of miRNAs, wherein said kit includes a reagent for detecting the internal reference gene set or the chip of claim 7 in a container,
   wherein said internal reference gene set includes let-7d+let-7g, let-7d+let-7i, or let-7d+let-7g+let-7i,
   said reagent is selected from the following group:
      (a) primers or pairs of the primers for specifically amplifying said internal reference gene set;
      (b) probes specifically hybridizing with nucleic acid molecules of said internal reference gene set,
   said chip is a nucleic acid chip and said chip has detection spots for specifically detecting nucleic acid molecules of said internal reference gene set.

9. A method for screening an internal reference gene for miRNA normalization, comprising:
   (1) obtaining samples, and extracting and quantifying miRNAs in the samples;
   (2) sequencing the miRNAs from the samples to obtain sequences of the miRNAs from the samples;
   (3) analyzing stability of the miRNAs, and selecting a miRNA with stability higher than the average level as a candidate reference gene.

10. The method of claim 4, wherein said internal reference gene set is let-7d+let-7g+let-7i, said internal reference gene set has less than 0.15 of an average expression stability M.

11. The kit of claim 8, wherein said internal reference gene set is let-7d+let-7g+let-7i, said internal reference gene set has less than 0.15 of an average expression stability M.

* * * * *

SEQUENCE LISTING

<160> NUMBER OF SEQ ID NOS: 3

<210> SEQ ID NO 1
<211> LENGTH: 22
<212> TYPE: RNA
<213> ORGANISM: Homo sapiens

<400> SEQUENCE: 1
agagguagua gguugcauag uu                                              22

<210> SEQ ID NO 2
<211> LENGTH: 22
<212> TYPE: RNA
<213> ORGANISM: Homo sapiens

-continued

```
<400> SEQUENCE: 2
ugagguagua guuuguacag uu                                              22

<210> SEQ ID NO 3
<211> LENGTH: 22
<212> TYPE: RNA
<213> ORGANISM: Homo sapiens

<400> SEQUENCE: 3
ugagguagua guuugugcug uu                                              22
```